United States Patent

Duerer

[11] Patent Number: 4,790,031
[45] Date of Patent: Dec. 13, 1988

[54] EYE SHIELD

[76] Inventor: Stormy W. Duerer, 4020 Bobbin La., Dallas, Tex. 75244

[21] Appl. No.: 912,535

[22] Filed: Sep. 29, 1986

[51] Int. Cl.⁴ .............................................. A61F 9/04
[52] U.S. Cl. ............................................. 2/15; 2/433; 2/439; 128/858
[58] Field of Search ...................... 2/15, 426, 431, 432, 2/433, 439, 446, 448, 454; 128/132 R, 163

[56] References Cited

U.S. PATENT DOCUMENTS

| | | | |
|---|---|---|---|
| D. 200,735 | 3/1965 | Mitchell | D16/103 |
| 1,274,257 | 7/1918 | Furlong | 2/433 |
| 1,553,010 | 9/1925 | Terry et al. | 2/15 |
| 1,886,725 | 11/1932 | Pedersen | 128/163 X |
| 2,072,183 | 3/1937 | Rentchler | 2/15 X |
| 2,165,668 | 7/1939 | Vaccaro | 2/15 |
| 2,305,080 | 12/1942 | Hemphill et al. | 2/15 |
| 2,527,947 | 10/1950 | Loos | 128/163 |
| 2,543,104 | 2/1951 | Golding | 2/15 R |
| 2,572,638 | 10/1951 | Loos | 128/163 |
| 2,642,569 | 6/1953 | Triebes et al. | 2/433 X |
| 2,874,385 | 2/1959 | Wade | 2/15 |
| 2,891,252 | 6/1959 | Lazo | 2/15 |
| 2,942,270 | 6/1960 | Enright | 2/15 |
| 3,092,103 | 6/1963 | Mower | 2/15 X |
| 3,541,608 | 11/1970 | Otwell | 2/15 |
| 4,024,405 | 5/1977 | Szot | 2/15 X |
| 4,068,918 | 1/1978 | Holcombe, Jr. | 350/1.5 |
| 4,162,542 | 7/1979 | Frank | 2/446 X |
| 4,331,136 | 5/1982 | Russell | 128/163 |
| 4,411,263 | 10/1983 | Cook | 128/132 R |
| 4,520,510 | 6/1985 | Daigle | 2/15 X |
| 4,546,493 | 10/1985 | Bortnick | 2/67 |

FOREIGN PATENT DOCUMENTS 101629  2/1917  United Kingdom .................. 2/433

*Primary Examiner*—W. C. Reynolds
*Attorney, Agent, or Firm*—Sigalos, Levine & Montgomery

[57] ABSTRACT

An eye shield formed of inner and outer layers of soft fabric with a flexible sun blocking material located between the inner and outer sheets of fabric for blocking total sun rays including harmful ultraviolet rays and having a relatively thick layer of soft material located between the inner and outer sheets of fabric to provide body to the mask-like portion and comfort to the wearer. The eye shield also includes a relatively small sight opening formed in each eye member and a semi-opaque lens plate extending across the eye member sight openings for blocking harmful ultraviolet rays. The sight opening may be located below the center of each eye member in order to prevent light rays from impinging directly on the eye of the wearer. In addition, portions of the straps forming the eye shield may be formed of material substantially transparent to ultraviolet tanning light rays such that the skin of the user may tan in those areas thereby avoiding white strap marks. Further, the head straps may include pockets formed in the outer end of each strap with a fine granulated material filling each of the pockets to form a weight for holding each strap gently against the sides of the head of the user when in the prone position.

12 Claims, 1 Drawing Sheet

EYE SHIELD

BACKGROUND OF THE INVENTION

The present invention relates generally to eye shields and in particular to an eye shield which is comfortable to the wearer, protects the wearers eyes from the harmful ultraviolet rays of the sun, enables the user to see through a sight opening that is covered with a dark material such as a sun glass lens, is constructed in the areas of the temples and the nose bridge of a material that is transparent to ultraviolet rays to prevent tanning marks and which may use a fine granulated material filling pockets in the outer ends of the head straps to form the weight to hold the eye shield gently against the eyes when the user is in the prone position.

It is customary to protect the eyes of the person exposed to the harmful effects of certain tanning rays such as ultra violet rays which are emitted from the sun or from sun lamps during sun tanning. This has been done heretofor by means of colored glasses or goggles worn on the head and covering the eyes. The goggles are used frequently by different customers and may become dirty or contaminated from such use and therefore likely to transmit germs from one person to another.

In addition, the goggles are not comfortable because they are generally made from a hard material such as plastic and may cause white streaks during tanning because of part of the plastic blocks the rays of the sun over the nose bridge and the temples of the wearer.

Other prior art devices utilize discardable protectors for each individual eye which are adapted to be placed over each eye and held in place by adhesive tabs attached thereto.

Still others utilize metallic inserts such as a layer of sheet aluminum having rubberized material coated on each side thereof and sandwiched between protective coatings.

Still other prior art devices utilize external plies of soft material and intermediate stiffening material to retain the shields in their proper form.

The present invention overcome the disadvantages of the prior art eye shields and provides an eye shield which is soft and pliable and conforms to the eyes of the wearer and yet provides total sun blocking in the area of the eyes.

The present invention also provides a sun shield with total sun blocking in the area of the eyes and having a relatively small sight opening formed in each eye member of the eye shield with a semi-opaque lens plate extending across the sight opening for blocking ultraviolet rays yet allowing the wearer to see through the plate and the sight opening.

The present invention provides an eye shield with total sun blocking in the area of the eyes and having a relatively small sight opening in the lower portion of the eye piece which is covered by a semi-opaque lens plate for preventing ultraviolet rays from entering and also preventing a substantial quantity of light rays from passing directly to eye but enabling the wearer to see by looking downwardly instead of directly outwardly.

The present invention also provides an eye shield with that portion of the head band lying adjacent to the temple areas and the nose bridge being formed of a material substantially transparent to ultraviolet rays such that the skin of the wearer in those areas may tan thereby avoiding white strap marks.

Further the present invention provides an eye shield which has a pocket formed in the outer end of each head strap with a fine granulated material filling each of the pockets thereby forming a weight to hold each strap gently against the sides of the head of the user when the user is in the prone position.

SUMMARY OF THE INVENTION

Thus the present invention relates to an improved eye shield of the type having a mask-like portion with two eye members and a nose bridge integrally formed with and interconnecting the eye members, each of the eye members being configured to conform to an eye socket of the wearer for shielding the eye with a minimum of facial coverage and means attached to the masklike portion for securing the eye members in place over the eyes, the improvement comprising an inner and an outer sheet of soft, lightweight fabric forming the mask-like portion, a flexible sun blocking material located between and encompassed by the inner and outer sheets of fabric for totally blocking the visible sun rays and ultraviolet rays, and a relatively thick layer of soft material located between said inner and outer sheets of fabric for providing body to the mask-like portion and comfort to the wearer.

The invention also relates to an improved eye shield in which a relatively small sight opening is formed in each eye member of the eye shield and a semi-opaque lens plate is located between the inner and outer sheets of fabric and extend across the eye member openings for blocking ultraviolet rays yet allowing the wearer to see through the lens plate and the eye openings.

The invention also relates to an improved eye shield having at least a portion of the head band lying adjacent the temple areas and the nose bridge area being formed of material substantially transparent to ultraviolet light such that the skin of the user in those areas may tan thereby avoiding white strap marks.

The invention further relates to an improved eye shield having pockets formed in the outer ends of each head strap with a fine, dense, granulated material filling each of the pockets to form a weight to hold each strap gently against the side of the head of the user when the user is in the prone position.

BRIEF DESCRIPTION OF THE DRAWINGS

These and other objects of the present invention will be disclosed more fully in conjunction with the accompanying drawings in which like numerals represent like components and in which.

DETAILED DESCRIPTION OF THE DRAWINGS

Figure 1:
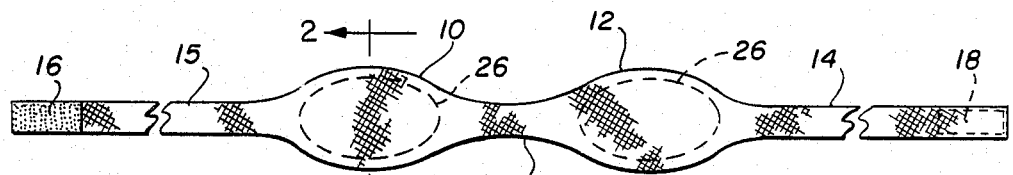
FIG. 1 is a plan view of the novel eye shield of the present invention.

FIG. 1 is a front view of the novel eye shield of the present invention and illustrates a mask-like portion having eye members 10 and 12 and a nose bridge portion 20 integrally formed with and interconnecting eye members 10 and 12. Each of the eye members 10 and 12 is configured to conform to an eye socket of the wearer shielding the eye with a minimum of facial coverage. Flexible head straps 14 and 15 are attached to opposite sides of the interconnected eye members 10 and 12 as shown and have a fastening means 16 and 18 on each end thereof for fastening the head straps 14 and 15 about the head if desired. Fastening means 16 and 18 could be velcro, a buckle, snap or the like.

The eye shield includes an inner and an outer sheet of soft, lightweight fabric such as cotton forming the mask-like portion and the head straps 14 and 15. A flexible sun blocking material 26 is located between and is emcompassed by the inner and outer sheets of fabric for blocking total visible sun rays and ultra-violet rays thereby protecting the eyes from harmful rays. This material 26 may be a fabric treated with rubber on both sides and which is chemically treated to block ultra-violet rays as is well-known in the art. Such fabric for instance is used as a backing for drapes to prevent sun bleaching.

Figure 2:
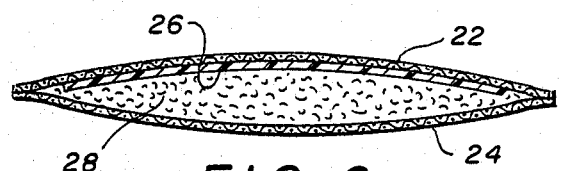
FIG. 2 is cross-sectional view of one lens of the eye shield shown in FIG. 1.

FIG. 2 is a cross-sectional view of the eye member portion 10 shown in FIG. 1 taken the long lines 2—2. As can be seen in FIG. 2, the eye member is substantially oval shaped in cross-section with outer and inner cotton fabric covers 22 and 24 respectively. The flexible sun blocking material 26 may be of any wellknown type which blocks the entire sun rays including ultraviolet rays. A relatively thick layer of soft material 28, such as felt, is located between and in substantially superimposed relationship with the sun blocking material 26 and the inner sheet of fabric 24. Of course, it could be provided and located between and in substantially superimposed relationship with the sun blocking material 26 and the outer sheet of fabric 22. It is more useful to place it on the inner side 24 since it would be closest to the eye of the user and provide the greatest comfort.

With the eye shield as disclosed in relation to FIGS. 1 and 2, the user has no vision whatsoever while wearing it. In the embodiment illustrated in FIG. 3 a relatively small sight opening 30 and 32 is formed in the eye members 11 and 13, respectively, of the eye shield and extends through inner fabric sheet 22, outer fabric sheet 24, sun blocking material 26 and soft material 28. A semi-opaque lens 34 and 36 is located between the inner and outer sheets of fabric 22 and 24 and extend across the small sight openings 30 and 32, respectively, for blocking ultraviolet rays and yet allowing the wearer to see through the lens plates 34 and 36 and the eye openings 30 and 32. Lens 34 and 36 may be plexiglass treated with ultraviolet blocking chemicals as is well-known in the art and has a thickness of approximately that of camera film. Thus it can be sewed into the fabric. This embodiment has all of the advantages of the device shown in FIG. 1 and FIG. 2 except that it now allows the wearer to have vision through the relatively small sight openings 30 and 32. However, in this embodiment, the light through the small sight openings 30 and 32 impinge directly upon the eyes of the user.

Thus the embodiment of FIG. 4 places the small sight openings 31 and 33 below the center of each eye member 17 and 19 of the mask-like portion such that a substantial quantity of light rays are prevented from passing directly to the eye but the wearer is allowed to see by looking downwardly instead of directly outwardly. Thus direct impingement of any light rays upon the eyes of the wearer is prevented with the embodiment illustrated in FIG. 4.

Figure 3:
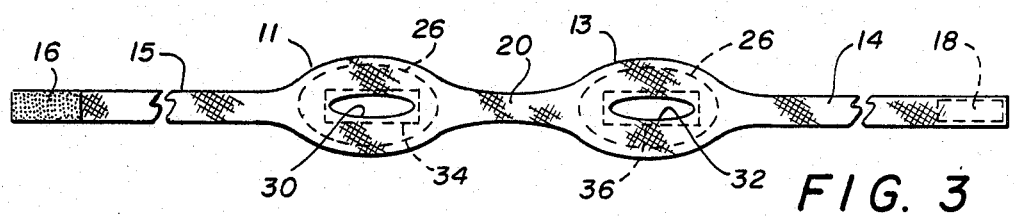
FIG. 3 is a plan view of an alternate embodiment of the novel eye shield of the present invention illustrating eye openings therein covered with a semi-opaque ultraviolet ray blocking material which allows the user to see through the eye openings but protects the eyes from ultraviolet rays.
Figure 4:
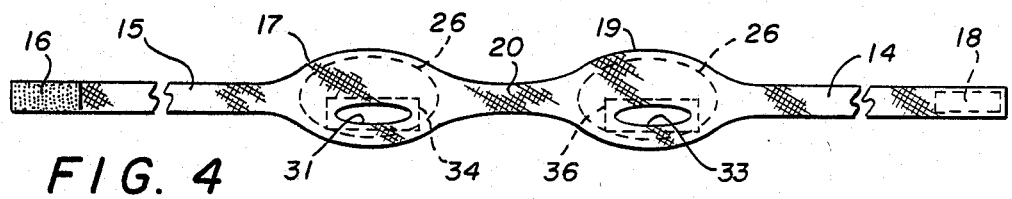
FIG. 4 is an alternate embodiment of the present invention in which the eye opening is located toward the bottom of the eye shield thereby preventing direct admittance of light to the eye but yet allowing the wearer thereof to see by looking downwardly.
Figure 5:
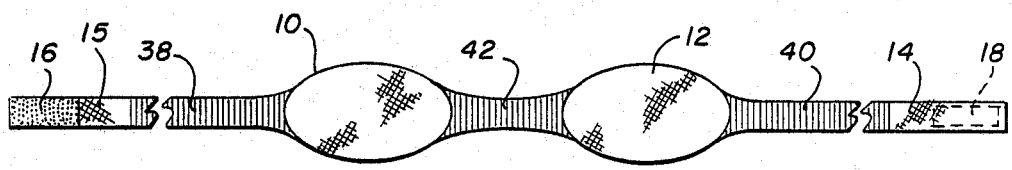
FIG. 5 is a plan view of another embodiment of the present invention in which those areas of the eye shield which cover the temple and nose bridge areas of the wearer is made of a material substantially transparent to ultraviolet light such that the skin of the wearer in those areas may tan thereby avoiding a white strap mark.

In either of the embodiments illustrated in FIGS. 1, 3 and 4, if the nose bridge connector 20 and straps 14 and 15 are formed of the construction illustrated in FIG. 2 except without the sun blocking material 26, white marks may be left across the bridge of the nose and the temples of the wearer because the straps alone do in fact block the tanning rays of the sun. In the embodiment shown in FIG. 5, at least that portion of the straps 14 and 15 lying in the areas 38 and 40 adjacent the temple areas and in the area 42 across the nose bridge are formed of a material substantially transparent to ultraviolet light such that the skin of the user may tan in those areas thereby avoiding white strap marks. Such material may be of the type which is transparent to tanning light rays with a wavelength below 400 nanometers.

Figure 6:
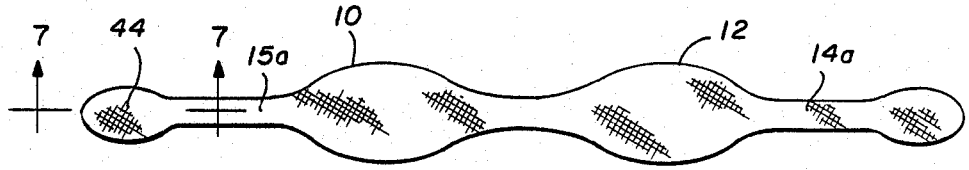
FIG. 6 is a plan view of the present invention in which a fine granulated material located in pockets in the outer ends of each head strap thereby forming a weight to hold each strap gently against the sides of the head when the wearer is in the prone position.
Figure 7:
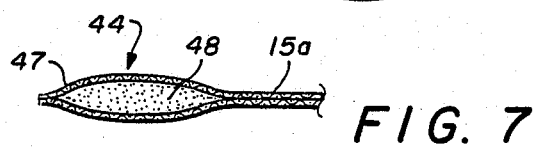
FIG. 7 is a cross-sectional view through a portion of the outer end of one of said head straps illustrated in FIG. 6 illustrating the pocket and the granulated material therein.

In addition, it may be desirable to allow the eye shield to rest comfortably upon the eyes while in the prone position without having the head straps 14 and 15 fastened tightly about the head. In the embodiment shown in FIG. 6, the ends 44 and 46 of the straps 14a and 15a are designed of such a length as to rest just above and back of the ears of the wearer. In addition, as shown in FIG. 7 these ends have a pocket 47 formed therein which is filled with a fine granulated material 48 such as sand which forms a weight on each end of the straps 14a and 15a thereby holding the straps comfortably in position behind the ears and thus keeping the eye pieces comfortably positioned against the eyes.

Thus there has been disclosed a new and improved eye shield consisting of eye members integrally formed with and connected to each other by a nose bridge and having straps attached on either side thereof for securing the eye members in place over the eyes and which is formed of inner and outer sheets of soft, light weight fabric with a flexible sun blocking material located between and encompassed by the inner and outer sheets of fabric for blocking total visible sun rays and ultraviolet rays which may be dangerous to the eye. In addition, a relatively thick layer of soft material is located between and in substantially superimposed relationship with the sun blocking material and one of the inner and outer sheets of fabric to provide body to the mask like portion and comfort to the wearer.

Also, one embodiment has relatively small sight openings formed in each eye member of the eye shield with a semi-opaque lens plate located between the inner and outer sheets of fabric and extending across the eye member openings for blocking ultra-violet rays harmful to the eye yet allowing the wearer to see through the lens plate and the corresponding eye openings.

In still another embodiment, the sight opening is located just below the center of each eye member of the mask-like portion with the semi-opaque lens covering each of the sight openings such that a substantial quantity of light rays are prevented from passing directly to the eye but allow the wearer to see by looking downwardly instead of directly outwardly.

In still another embodiment, that portion of the head band lying against the temple areas and across the nose bridge are formed of material substantially transparent to ultraviolet light tanning rays such that the skin of the user may tan in those areas thereby avoiding white strap marks.

Finally, pockets may be formed in the outer end of each head strap with a fine granulated material filling those pockets thereby forming a weight to hold each strap gently against the sides of the head of the user when in the prone position.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined in the appended claims.

I claim:

1. In an eye shield of the type having a mask-like portion with two eye members and a nose bridge integrally formed with and interconnecting said eye members, each of said eye members being configured to conform to an eye socket of the wearer for shielding the eye for a minimum of facial coverage and means attached to the mask-like portion for securing said eye members in place over the eyes, the improvement comprising;
   a. an inner and an outer sheet of soft, light-weight fabric forming said mask-like portion;
   b. a flexible sun blocking material located between and encompassed by said inner and outer sheets of fabric for totally shielding the eyes from visible sun rays and harmful ultraviolet rays,
   c. a relatively thick layer of soft material located between said inner and outer sheets of fabric for providing body to said mask-like portion and comfort to said wearer,
   d. a relatively small sight opening formed in each eye member in each eye shield, and
   e. a semi-opaque lens plate located between said inner and outer sheets of fabric and extending across said eye member openings for blocking harmful ultraviolet rays yet allowing the wearer to see through said lens plate and said eye openings.

2. An improved eye shield as in claim 1 further comprising each eye member of said mask-like portion having said sight opening located below the center of said eye member such that a substantial quantity of light rays is prevented from passing directly to the eye but enables the wearer to see by looking downwardly instead of directly outwardly.

3. An improved eye shield as in claim 2 wherein said securing means attached to said mask-like portion of said eye shield comprises:
   a. a flexible head band attached to opposite sides of said interconnected eye members, and
   b. at least that portion of said head band lying adjacent to temple areas of the wearer being formed of material substantial transparent to ultraviolet tanning light rays such that the skin of the wearer may tan in the temple areas thereby avoiding white strap marks.

4. In an eye shield of the type having a mask-like portion with two eye members and a nose bridge integrally formed with and interconnecting said eye members, each of said eye members being configured to conform to an eye socket of the wearer for shielding the eye for a minimum of facial coverage and means attached to the mask-like portion for securing said eye members in place over the eyes, the improvement comprising;
   a. an inner and an outer sheet of soft, lightweight fabric forming said mask-like portion,
   b. a flexible sun blocking material located between and encompassed by said inner and outer sheets of fabric for totally shielding the eyes from visible sun rays and harmful ultraviolet rays,
   c. a relatively thick layer of soft material located between said inner and outer sheets of fabric for providing body to said mask-like portion and comfort to said wearer,
   d. a flexible head band attached to opposite sides of said interconnected eye members, and
   e. at least that portion of said head band lying adjacent to temple areas of the wearer being formed of material substantially transparent to ultraviolet tanning light rays such that the skin of the wearer may tan in the temple areas thereby avoiding white strap marks.

5. An improved eye shield as in claim 4 wherein said securing means attached to said mask-like portion of said eye shield further comprises:
   a. a flexible strap attached to opposite sides of said interconnected eye members and having a length extending just beyond each ear,
   b. a pocket formed in the outer end of each strap, and
   c. a fine granulated material filling each of said pockets thereby forming a weight to hold each strap gently against the sides of the head of the user when in the prone position.

6. An improved eye shield as in claim 4 further comprising means for forming said nose bridge of a material substantially transparent to ultraviolet tanning light rays such that the skin of the wearer in the nose bridge area may tan thereby avoiding a white strap mark over the bridge of the nose.

7. In a method of forming an eye shield of the type having a mask-like portion with two eye members and a nose bridge integrally formed with and interconnecting said eye members, each of said eye members being configured to conform to an eye socket of the wearer for shielding the eye with a minimum of facial coverage and securing the eye members in place over the eyes with means attached to the mask-like portion, the improvement comprising the steps of:
   a. forming said mask-like portion of an inner and an outer sheet of soft, light weight fabric,
   b. locating a flexible sun blocking material between said inner and outer sheets of fabric for totally shielding the eyes from visible sun rays and harmful ultraviolet rays,
   c. locating a relatively thick layer of soft material between said inner and outer sheets of fabric for providing body to said mask-like portion and comfort to said wearer, d. forming a relatively small sight opening in each eye member of said eye shield, and
e. locating a semi-opaque lens plate between said inner and outer sheets of fabric and extending across said eye member openings for blocking harmful ultraviolet rays yet allowing the wearer to see through said lens plate and said eye openings.

8. A method as in claim 7 further comprising the steps of locating said sight opening covered by said semi-opaque lens plate below the center of such eye member of said mask-like portion such that a substantial quantity of light rays is prevented from passing directly to the eye but enables the wearer to see by looking downwardly instead of directly outwardly.

9. A method as in claim 8 wherein the step of attaching said securing means to the mask-like portion of the eye shield further comprises the steps of:
   a. attaching a flexible head band to opposite sides of said interconnected eye members, and
   b. forming at least that portion of said head band lying adjacent to temple areas of material substantially transparent to ultraviolet tanning light rays such that the skin of the wearer may tan in the temple areas thereby avoiding white strap marks.

10. In a method of forming an eye shield of the type having a mask-like portion with two eye members and a nose bridge integrally formed with and interconnecting said eye members, each of said eye members being configured to conform to an eye socket of the wearer for shielding the eye with a minimum of facial coverage and securing the eye members in place over the eyes with means attached to the mask-like portion, the improvement comprising the steps of:
   a. forming said mask-like portion of an inner and an outer sheet of soft, light weight fabric,
   b. locating a flexible sun blocking material between said inner and outer sheets of fabric for totally shielding the eyes from visible sun rays and harmful ultraviolet rays,
   c. locating a relatively thick layer of soft material between said inner and outer sheets of fabric for providing body to said mask-like portion and comfort to said wearer,
   d. attaching a flexible head band to opposite sides of said interconnected eye members, and
   e. forming at least that portion of said head band lying adjacent to temple areas of material substantially transparent to ultraviolet tanning light rays such that the skin of the wearer may tan in the temple areas thereby avoiding white strap marks.

11. An improved method as in claim 9 or 10 further comprising the steps of:
   a. forming said flexible strap of a length extending just beyond each ear,
   b. forming a pocket in the outer end of each strap, and
   c. filling each of said pockets with a fine granulated material thereby forming a weight to hold each strap gently against the sides of head of the wearer when in the prone position.

12. An improved method as in claim 9 or 10 further comprising the step of forming said nose bridge of a material substantially transparent to ultraviolet tanning light rays such that the skin of the wearer in the nose bridge area may tan thereby avoiding a white strap mark over the bridge of the nose.

* * * * *